(12) United States Patent
Lin et al.

(10) Patent No.: US 9,091,683 B2
(45) Date of Patent: Jul. 28, 2015

(54) METHOD FOR FABRICATING A BIOSENSOR CHIP AND THE BIOSENSOR CHIP MADE THEREBY

(71) Applicants: Kuan-Jiuh Lin, Taichung (TW); Chuen-Yuan Hsu, Yunlin County (TW)

(72) Inventors: Kuan-Jiuh Lin, Taichung (TW); Chuen-Yuan Hsu, Yunlin County (TW)

(73) Assignee: NATIONAL CHUNG-HSING UNIVERSITY, Taichung (TW)

( * ) Notice: Subject to any disclaimer, the term of this patent is extended or adjusted under 35 U.S.C. 154(b) by 117 days.

(21) Appl. No.: 13/854,847

(22) Filed: Apr. 1, 2013

(65) Prior Publication Data

US 2013/0230427 A1 Sep. 5, 2013

Related U.S. Application Data

(62) Division of application No. 12/858,959, filed on Aug. 18, 2010, now Pat. No. 8,663,554.

(30) Foreign Application Priority Data

Aug. 19, 2009 (TW) ................................ 98127852 A

(51) Int. Cl.
  *G01N 33/53* (2006.01)
  *B82Y 5/00* (2011.01)
  *B82Y 15/00* (2011.01)

(52) U.S. Cl.
  CPC . *G01N 33/53* (2013.01); *B82Y 5/00* (2013.01); *B82Y 15/00* (2013.01)

(58) Field of Classification Search
  CPC ........... G01N 33/53; B82Y 5/00; B82Y 15/00
  USPC ......................................................... 422/425
  See application file for complete search history.

(56) References Cited

U.S. PATENT DOCUMENTS

| | | | |
|---|---|---|---|
| 2003/0215816 A1 | 11/2003 | Sundararajan et al. | |
| 2004/0197845 A1 | 10/2004 | Hassibi et al. | |
| 2007/0285657 A1 * | 12/2007 | Wang et al. | 356/301 |
| 2008/0008844 A1 | 1/2008 | Bettge et al. | |
| 2008/0220982 A1 * | 9/2008 | Vu | 506/9 |
| 2009/0191356 A1 | 7/2009 | Lee et al. | |
| 2010/0048029 A1 | 2/2010 | Kumar et al. | |
| 2010/0086439 A1 | 4/2010 | Yamanaka et al. | |
| 2010/0164489 A1 * | 7/2010 | Lukaszew et al. | 324/244.1 |

OTHER PUBLICATIONS

Yuan et al., An electrochemical enzyme bioaffinity electrode based on biotin-streptavidin conjunction and bienzyme substrate recycling for amplification, 2010, Analytical Biochemistry, 405, p. 121-126.*

* cited by examiner

*Primary Examiner* — Lore Jarrett
(74) *Attorney, Agent, or Firm* — Holland & Hart LLP

(57) ABSTRACT

A method of fabricating a biosensor chip includes: forming at least one metallic layer on a transparent substrate to form a composite member; disposing the composite member in a vacuumed chamber, and introducing a gas into the vacuumed chamber; applying microwave energy to the gas to produce a microwave plasma of the gas within the vacuumed chamber, and causing the microwave plasma to interact with the metallic layer so that the metallic layer is melted and formed into a plurality of metallic nanoparticles that are spaced apart from each other and that expose partially the surface of the transparent substrate; and disposing a receptor at the surface of the transparent substrate that is exposed among the metallic nanoparticles. A biosensor chip is also disclosed.

8 Claims, 14 Drawing Sheets

METHOD FOR FABRICATING A BIOSENSOR CHIP AND THE BIOSENSOR CHIP MADE THEREBY

CROSS-REFERENCE TO RELATED APPLICATION

This application is a divisional of prior U.S. patent application Ser. No. 12/858,959, filed on Aug. 18, 2010, which claims priority to Taiwanese Application No. 098127852, filed on Aug. 19, 2009, the entire contents of which are incorporated herein by reference.

BACKGROUND OF THE INVENTION

1. Field of the Invention

The invention relates to a method for fabricating a biosensor chip, and more particularly to a method for fabricating a biosensor chip utilizing nano-technology. The invention also relates to a biosensor chip made by the method.

2. Description of the Related Art

There are various chemo-sensors, for example, a taste sensor, a smell sensor, a hormone receptor of an endocrine system, a chemical transmitter substance and a receptor protein of a neutron-transmitting system, an antibody or an antigen of an immune system, or the like, in an organism so as to form an assembly of chemo-receptors in the organism. The existence of a specific, substance or molecule and the specific physiological reaction produced thereby may be detected using a specific selection and sensitivity of a specific one of the chemo-receptors to the specific substance or molecule.

A biosensor chip is developed utilizing the aforesaid principle. A receptor molecule or substance mounted on a specific material or device forms a specific bonding to a substance to be detected, a physical or chemical measurement is conducted, and a concentration of the substance to be detected is determined according to the measurement. The biosensor chip is primarily composed of a receptor which has a specific bonding capability for a substance to be detected, and a substrate which will produce variation in charge, thickness, mass, optical properties, or the like when the receptor bonds to the substance to be detected. Therefore, the biosensor chip can be used for detecting a specific substance and the concentration thereof by using a specific receptor which has a specific bonding capability for the specific substance to be detected and a variation of a specific physical property.

A conventional biosensor chip is produced on a silicon substrate using a semiconductor process. The process is relatively complicated and costly. Detection error will increase after repeated use as a result of damage during a cleaning procedure. The structure of the conventional biosensor chip is liable to be affected when detection is conducted in a solution, which may result in signal interference and unstable detection result. Therefore, the conventional biosensor chip is disadvantageous in terms of detection stability and durability.

Because nano-materials have specific characteristics in size and physical properties, they have been applied to the biosensor chip so as to improve structure/stability and sensitivity of the biosensor chip and to provide the biosensor chip with better durability and detection sensitivity and precision.

Nano-material usually includes nanoparticles, nanofiber, nano-film, and nano-bulk. Among others, since nanoparticles have been developed for a longer period of time, technologies thereof are more mature than others. Further, as nanofiber and nano-film are made from nanoparticles, production of nanoparticles is relatively important. In general, methods of producing nanoparticles may be classified into physical method and chemical method.

A major example of the chemical method is chemical reduction. In the chemical reduction, nanoparticles are formed through reduction of metal ions in a solution, to which a protecting agent is added so as to maintain uniform distribution of the nanoparticles in the solution and prevent aggregation of the nanoparticles. After the nanoparticles are covered by the protecting agent, a substrate, which has a surface disposed with an organic functional group, is provided for formation of a self-assembly nanostructure, such nanoparticles, thereon through static attraction force and chemical bonding therebetween. Solutions containing organic materials, such as toluene and thiol-containing organic molecules, are usually used in the chemical reduction. However, the organic materials are likely to contaminate the environment and are harmful to human health.

Examples of physical methods for producing nanoparticles include high temperature annealing, electron beam irradiation heavy on irradiation, pulsed laser irradiation, and nanolithography. In the first four of the aforesaid physical methods, a thin film is heated so as to form cracks, become discontinuous, and be melted. Thereafter, spherical nanoparticles are formed by surface tension forces. In the last one of the aforesaid physical methods, a substrate is covered by a specific mask. For example, nano-scale silicon particles are arranged in a hexagonal closed-packed structure. Subsequently, a metal is deposited on interstices of the hexagonal closed-packed structure such that the nanoparticles are formed and arranged in a triangular array. However, the above-mentioned five physical methods have the following disadvantages.

In the high temperature annealing method, raising and lowering of temperature require a long period of time, which results in time-consumption and lower efficiency, and non-uniform morphology and easy aggregation of the nanoparticles.

In the electron beam Irradiation method, expensive equipment, such as an electron gun, is needed. In addition, since an electron beam generated from the electron gun can merely focus on a limited region on the substrate in each operation, a long time is required for producing nanoparticles on the substrate having a large area. Thus, the method is also less effective.

In the heavy ion irradiation method, the disadvantages are similar to those in the electron beam irradiation method, and the application thereof is still limited to academic study.

The pulsed laser irradiation method is also less effective because a laser source can irradiate only a small region of the substrate and needs to move back and forth to treat a large area of the substrate.

In the nanolithography method although mass production of nanoparticles is possible, the method is complicated and time-consuming, and requires organic solvents to clean the substrate, which is not environmentally friendly.

The structure and the production efficiency of the substrate for the conventional biosensor chip may be improved by cooperating with a novel method for producing nanoparticles. In addition to reducing the production cost, the amount of the target material may be detected by utilizing the characteristics of the nanoparticles to provide physical variation required for the biosensor chip, thereby producing an effect better than that of the conventional biosensor chip.

There are researches directed to disposal of receptors on surfaces of metallic nanoparticles to detect a target material via variation of spectrum signal of the metallic nanoparticles.

However, when the receptors disposed on the surfaces of the metallic nanoparticles have relatively large thickness, for example, when it is required to dispose layers of molecules for forming the receptors on the surfaces of the metallic nanoparticles, the target material to be detected is the relatively far from the metallic nanoparticles, which results in the disadvantage in which variation of the spectrum signal of the metallic nanoparticles is less sensitive for detecting whether the target material bonded to the receptors or not.

SUMMARY OF THE INVENTION

An object of the present invention is to provide a method for fabricating a biosensor hip which can bond with a target analyte and which can detect the target analyte with improved sensitivity.

Another object the present invention is to provide the biosensor chip for detecting a target analyte.

In one a aspect of this invention, a method of fabricating biosensor chip includes; forming at least one metallic layer on a transparent substrate to form a composite member; disposing the composite member in a vacuumed chamber, and introducing a gas into the vacuumed chamber; applying microwave energy to the gas to produce a microwave plasma of the gas within the vacuumed chamber, and causing the microwave plasma to interact with the metallic layer so that the metallic layer is melted and formed into a plurality of metallic nanoparticles that are spaced apart from each other and that expose partially the surface of the transparent substrate; and disposing a receptor at the surface of the transparent substrate that is exposed among the metallic nanoparticles.

In another aspect of the present invention, a biosensor chip for detecting a target analyte includes a transparent substrate metallic nanoparticles formed on a surface of the transparent substrate in a spaced apart, manner, a surface-modifier attached to the surface of the transparent substrate among the metallic nanoparticles, and an analyte-specific receptor bound to the surface-modifier.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
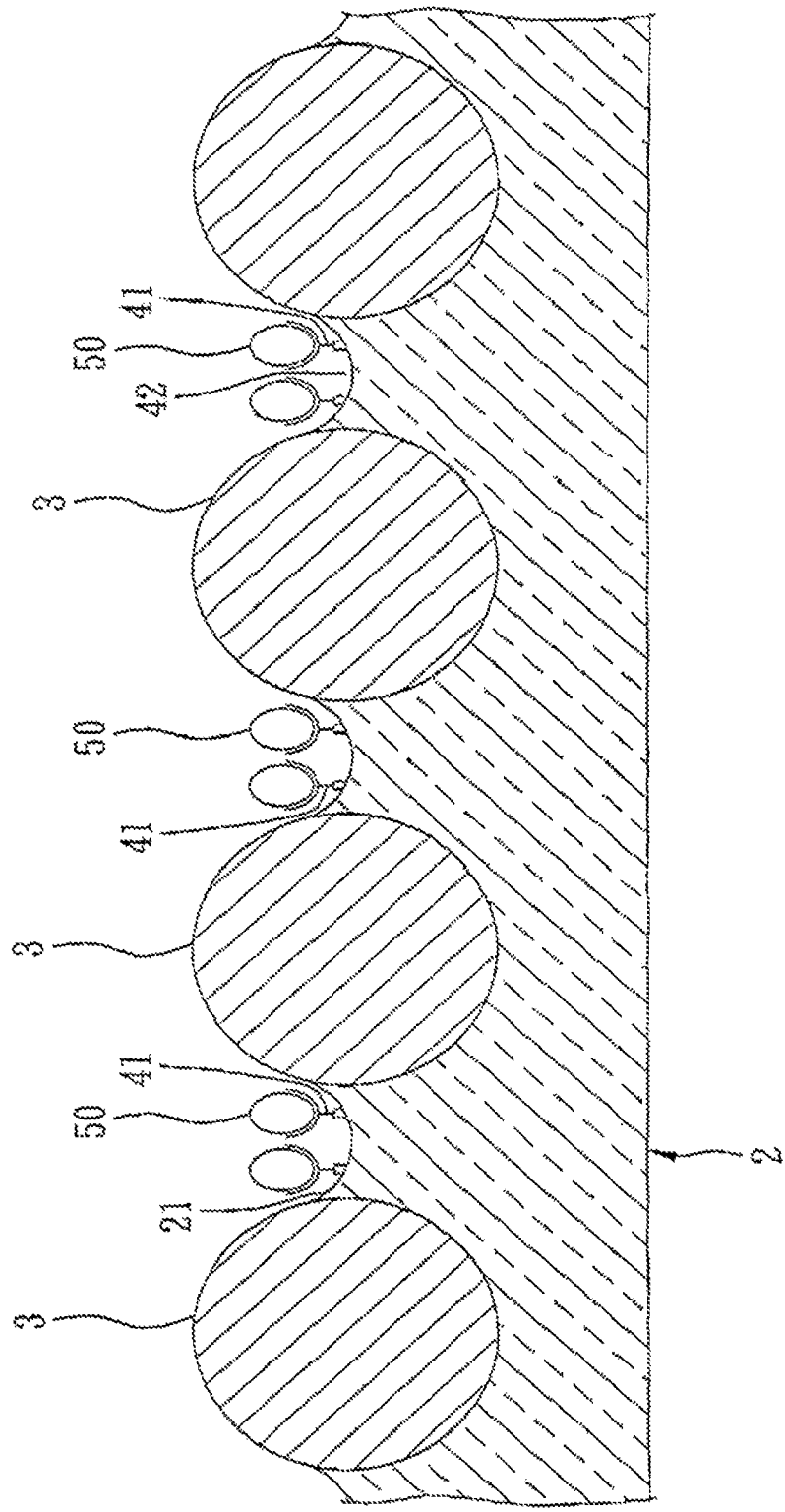
FIG. 1 is a fragmentary schematic view of a preferred embodiment of a biosensor chip according to the present invention.

Referring to FIG. 1, the preferred embodiment of a biosensor chip according to the present invention is used for detecting a target analyte 50, and includes a transparent substrate 2, metallic nanoparticles 3 formed on a surface 21 of the substrate in a spaced apart manner surface-modifiers 42 attached to the surface 21 of the substrate 2 among the metallic nanoparticles 3, and analyte-specific receptors 41 bound to the surface-modifiers 42.

The transparent substrate 2 is preferably made from quartz, mica, sapphire, or transparent ceramics.

The metallic nanoparticles 3 are partly embedded in the transparence substrate 2, and have an average diameter ranging from 5 nm to 20 nm, and preferably from 10 nm to 20 nm, and are preferably made from gold, silver, or an alloy of gold. Since gold has stable physical and chemical properties the metallic nanoparticles 3 are more preferably made from gold.

The target analyte 50 suitable for detection by the biosensor chip of the present invention includes biochemical molecules and heavy metal ions. The suitable material useful as the analyte-specific receptors 41 is selected according to the target analyte 50 to be detected. For example, when the target analyte 50 to be detected is streptavidin biotin is selected as the analyte-specific receptors 41 because biotin binds specifically to streptavidin. Since biotin can not bind directly to the surface 21 of the substrate 2, aminopropyltrimethoxysilane (abbreviated as APTMS hereinafter) is used as the surface modifiers 42 for attaching to the surface 21 of the substrate 2 because APTMS can bind to the surface 21 of the substrate 2 easily and can bind to biotin as well. Therefore, a film of APTMS used as the surface-modifiers 42 is attached to the surface 21 of the substrate 2 among the metallic nanoparticles 3, and biotin used as the analyte-specific receptors 41 is bound to the film of APTMS. Therefore, streptavidin can be detected by the biosensor chip of the present embodiment by utilizing the specific binding property of biotin to streptavidin.

When the target analyte 50 to be detected is anti-immunoglobulin G (anti-IgG) IgG is selected as the analyte-specific receptors 41. APTMS bound to glutaraldehyde is used as the surface modifiers 42 for attaching to the surface 21 of the substrate 2 via APTMS and for binding with IgG via glutaraldehyde. Therefore, a combination of APTMS and glutaraldehyde used as the surface-modifiers 42 is attached the surface 21 of the substrate 2 among the metallic nanoparticles 3 and IgG used as the analyte-specific receptors 41 is bound to glutaraldehyde. Therefore, can be detected by the biosensor chip of the present embodiment by utilizing the specific binding property of IgG to anti-IgG.

When the target analyte 50 to be detected is mercurous ions, 4-carboxybenzo-15-crown-5 is selected as the analyte-specific receptors 41 because 4-carboxybenzo-15-crown-5 specifically binds to the mercurous ions. A silane compound such as aminopropyltrimethoxysilane is used as the surface modifiers 42 for attaching to the surface 21 of the substrate 2 and for binding with 4-carboxybenzo-15-crown-5. Therefore, a film of the silane compound used as the surface-modifiers 42 is attached to the surface 21 of the substrate 2 among the metallic nanoparticles 3, and 4-carboxybenzo-15-crown-5 used as the analyte-specific receptors 41 is bound to the film of the silane compound. Therefore, mercurous ions can be detected by the biosensor chip of the present embodiment by utilizing the specific binding property of 4-carboxybenzo-15-crown-5 to mercurous ions.

In order to permit the target analyte 50 to gain access to the analyte-specific receptors 41, the gaps among the metallic nanoparticles 3 are preferably larger than the size of the target analyte 50. However, if the gaps among the metallic nanoparticles 3 are too large, the sensitivity the biosensor chip may be unsatisfactory.

Extinction of localized surface plasmon resonance may vary according to particle size, particle shape, distances among particles, and dielectric constant of surrounding environment of the metallic nanoparticles 3 formed on the surface 21 of the substrate 2 (K. A. Willets, R. P. Van Duyne; Localized Surface Plasmon Resonance Spectroscopy and Sensing; *Ann. Rev. Phys. Chem.*, 2006, 58, 267). Therefore, when the target analyte 50 to be detected is bound to the analyte-specific receptors 41, variation of localized electromagnetic field of the metallic nanoparticles 3 induced by the irradiation of an incident light of specific frequency is affected by the surrounding environment of the metallic nanoparticles 3. Peak strength of extinction spectrum of localized surface plasmon resonance will vary accordingly. Therefore, whether a sample contains the target analyte 50 or not can be detected by the variation of extinction strength. Furthermore, the concentration of the target analyte 50 can be determined by the amount of variation of extinction strength so as to achieve an effect of quantitative analysis. Herein, the extinction is a reduction of strength of light after being absorbed by the substrate 2 and being scattered by the surface of the target analyte 50 as compared to incident light. Since the extinction attributed to scattering by the surface of the target analyte 50 is minimal, the extinction spectrum can be deemed as an absorption spectrum of the light absorbed by the substrate 2. Therefore, in the following description, the extinction spectrum is used to indicate the absorption spectrum of the light absorbed by the substrate 2.

Polarization rate is defined as a variation of dipole moment per unit volume of the metallic nanoparticles 3 under an action of an external electric field. When the biosensor chip of the present invention is irradiated by an incident light of specific frequency (deemed as an external electromagnetic field), the outer electrons of the metallic nanoparticles 3 will produce collectively dipolar oscillation, and thus produce an extinction of specific spectrum (so as to form a localized electromagnetic field). Once the outer electrons of the metallic nanoparticles 3 are affected by the external environment, the oscillation frequency will vary. For example, if the outer electron cloud of the metallic nanoparticles 3 is attracted, the dipole moment is lengthened the polarization rate is increased, the localized electromagnetic field is raised, and the signal strength of the extinction spectrum is varied.

It should be noted that after the detection is completed using the biosensor chip of the present invention, the biosensor chip may be cleaned using a proper buffer solution. For example, Glycine-HCl buffer solution may be used for dissociating streptavidin from biotin.

Figure 2:
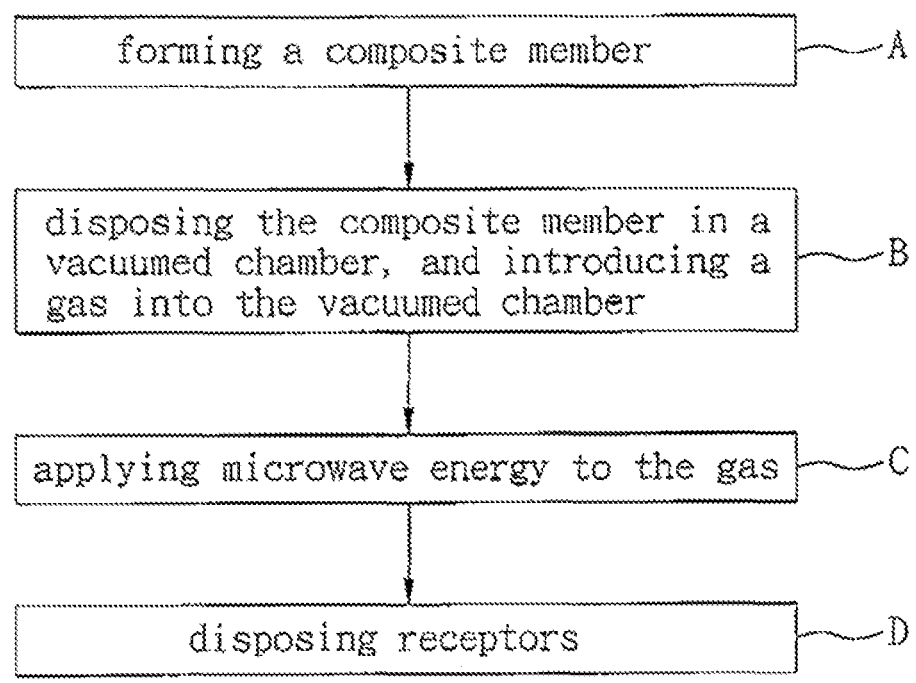
FIG. 2 is a flow chart of a preferred embodiment of a method of fabricating a biosensor chip according to the present invention.
Figure 3:
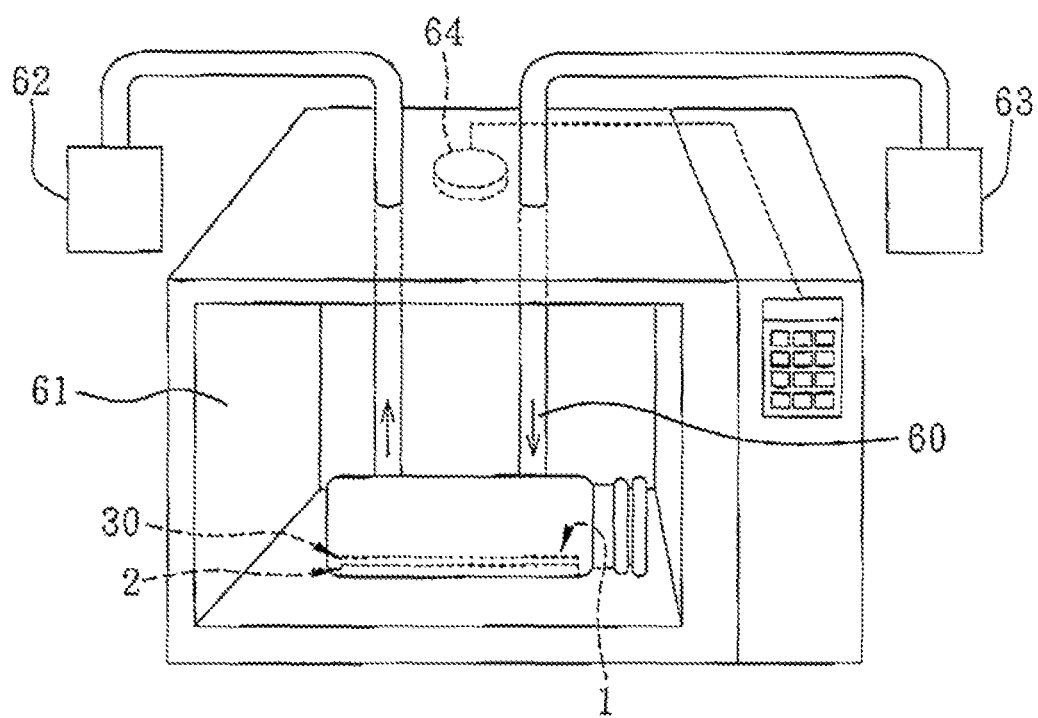
FIG. 3 is a schematic perspective view of an apparatus used in the preferred embodiment of FIG. 2.
Figure 4:
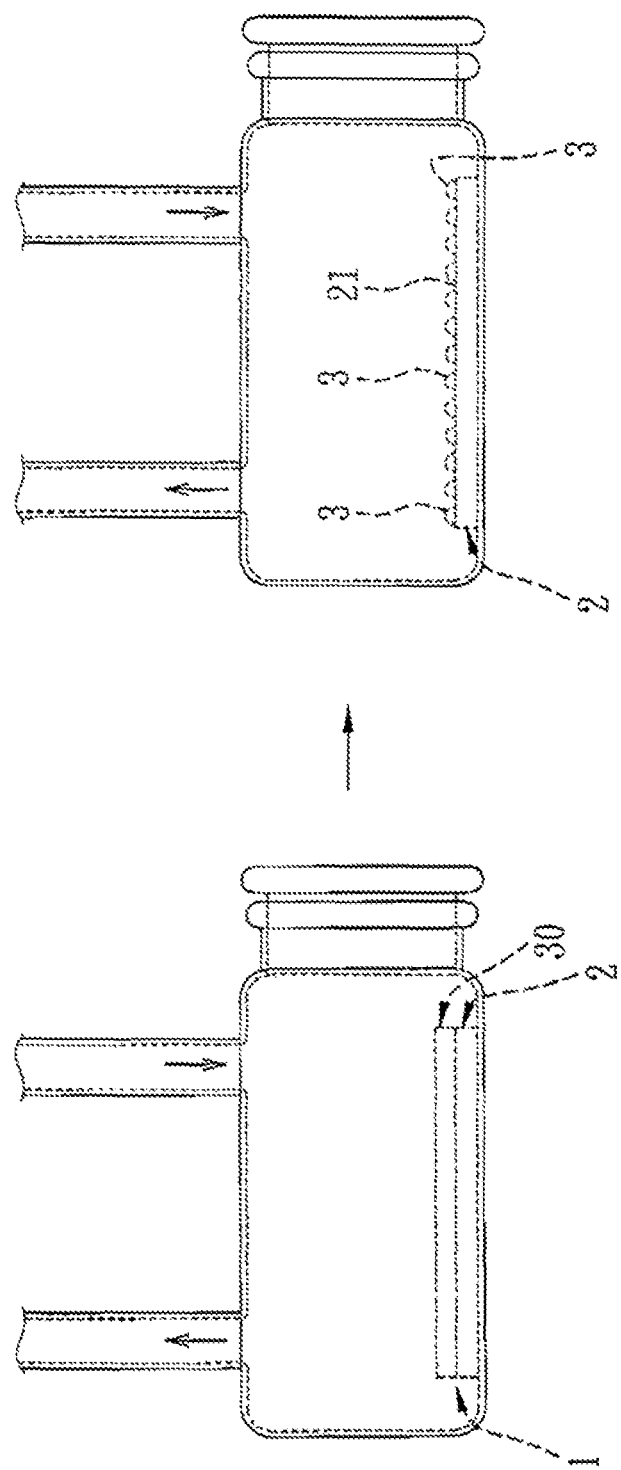
FIG. 4 is a schematic view illustrating a step of for nanoparticles in the preferred embodiment.

Referring to FIGS. 2, 3, and 4, the preferred embodiment of a method of fabricating a biosensor chip according to the present invention includes the steps of:

A) forming a composite member:

A composite member is formed by forming at least one metallic, layer 30 of a predetermined thickness on a transparent substrate 2. The metallic layer 30 is preferably made from gold, silver, or an alloy of gold. Since gold has stable physical and chemical properties, the metallic layer 30 is more preferably made from gold. As described above, the transparent substrate 2 is preferably made from glass, quartz, mica, sapphire, or transparent ceramics.

In the preferred embodiment, the metallic layer 30 of a predetermined thickness is formed on the transparent substrate 2 via a sputter coating technique accompanied with a film thickness measure. Since such technique is well known, details thereof will not be described.

B) disposing the composite member in a vacuumed chamber, and introducing a gas into the vacuumed chamber:

The composite member 1 is disposed in a vacuumed chamber 61, which is vacuumed using a vacuuming unit 62, and a gas 60 is introduced into the vacuumed chamber 61 using a gas supplying unit 63. In the preferred embodiment, the vacuumed chamber 61 is maintained at a pressure ranging from 0.2 torr to 6.0 torr. The gas 60 is selected from a group consisting of argon, nitrogen, and oxygen according to the specific requirement.

C) applying microwave energy to the gas:

Microwave energy is applied to the gas 60 for a predetermined period to produce a microwave plasma of the gas 60 within the vacuumed chamber 61. The microwave plasma interacts with the metallic layer 30 so that the metallic layer is melted and formed into a plurality of metallic nanoparticles 3 that are spaced apart from each other and that expose partially the surface 21 of the substrate 2. The particle size of the metallic nanoparticles 3 may be increased by increasing the thickness of the metallic layer 30. In the preferred embodiment, the thickness of the metallic layer 30 ranges preferably from 1 nm to 3 nm. The particle size of the metallic nanoparticles 3 can be controlled in a range from 5 nm to 20 mm by controlling the thickness of the metallic layer 30. Additionally, the period for applying microwave energy may be adjusted according to the thickness and/or the area of the metallic layer 30. That is, a longer period for applying microwave energy is required for a larger thickness or area of the metallic layer 30 so as to apply sufficient energy for melting the metallic layer 30. In the preferred embodiment, a microwave emitting unit 64 is used to apply microwave energy. The output power of the microwave emitting unit 64 preferably ranges from 700 W to 1500 W. In the preferred embodiment, the output power of the microwave emitting unit 64 is set to be 1100 W, and the frequency of the microwave emitting unit 64 is set to be 2430 MHz.

When it is intended to form the metallic nanoparticles 3 of an alloy, a plurality of metallic layers 30 made from different metals can be formed on the transparent substrate 2. Microwave energy is then applied to produce a microwave plasma. The microwave plasma interacts with the metallic layers 30 so that the metallic layers 30 are melted and formed into a plurality of metallic nanoparticles 3 of alloy. For example, when it is intended form the metallic nanoparticles alloy of gold and silver, a gold layer and a silver layer are formed on the transparent substrate 2. Microwave energy is then applied to produce a microwave plasma. The microwave plasma interacts with the gold and silver layers so that the gold and silver layers are melted and formed into a plurality of metallic nanoparticles 3 the alloy of gold and silver. The total thickness of the metallic layers 30 still should be controlled to be in a range from 1 nm to 3 nm. The thickness of each of the met layers 30 may be adjusted according to alloying ratio of the metals contained in the metallic nanoparticles 3, and preferably ranges from 0.1 nm to 2.9 nm.

The optical characteristics of the metallic nanoparticles 3 vary according to the particle size and constituents of the metallic nanoparticles 3. That is, a peak wavelength of an extinction spectrum varies according the particle size and the constituents of the metallic nanoparticles 3. For example, when the mean particle size of the metallic nanoparticles 3 ranges from 5 nm to 20 nm, the peak wavelength of the extinction spectrum will generally fall in a range from 400 nm to 650 nm. However, on the other hand, when the metallic nanoparticles 3 are formed from a gold layer having a thickness of 3 nm, the peak wavelength of the extinction spectrum ranges from 510 nm to 540 nm. When the metallic nanoparticles 3 are formed from a metallic layer that is an alloy of gold and silver and that has a thickness of 3 nm, the peak wavelength of the extinction spectrum ranges from 410 nm to 490 nm.

D) disposing receptors:

Referring again to FIG. 1, receptors 41 are disposed at the surface 21 of the substrate 2 that is exposed among the metallic nanoparticles 3. Specifically, radio-frequency atmosphere plasma is applied to the surface 21 of the substrate 2 to conduct a hydrophilic treatment. The surface 21 of the substrate 2 is modified using a surface-modifier 42 after the hydrophilic treatment. The receptors 41 are attached to the surface-modifier 42 by immersing the substrate 2 in a solution of the receptors 41.

The following examples are provided to illustrate the merits of the preferred embodiment of the invention, and should not be construed as limiting the scope of the invention.

Example 1

Forming Metallic Nanoparticles of Different Particle Sizes from Metallic Layers of Different Thicknesses 8 glass substrates of same dimension were treated via ultrasonication in acetone, ethanol, and deionized water sequentially for five minutes in each of the liquids to remove dust, and were dried using nitrogen. The glass substrates were immersed in a piranha solution to solution obtained by mixing $H_2SO_4$ with $H_2O_2$ in a 3:1 ratio) at a temperature of 80° C. for 30 minutes to remove organic residue, were rinsed with deionized water, and were dried using nitrogen. Each of the glass substrates was formed with a gold layer thereon in a sputter coater. A film thickness measure was used to control the thickness of the gold layer. The thicknesses of the gold layers formed on the glass substrates were 1 nm, 2 nm, 3 nm, 4 nm, 5 nm, 6 nm, 7 nm, and 8 nm, respectively.

Each of the glass substrates formed with gold layers thereon was disposed in a vacuumed chamber, which was vacuumed using a vacuuming unit, and argon was introduced into the vacuumed chamber using a gas supplying unit. The vacuumed chamber was maintained at a pressure of 0.3 torr.

Microwave energy was applied to argon to produce a microwave plasma of argon within the vacuumed chamber. The microwave plasma interacted with the gold layer so that the gold layer was melted and formed into a plurality of gold nanoparticles that are spaced apart from each other and that exposed partially the surface of the glass substrate. The period for applying microwave energy was adjusted according to the thickness of the gold layer. The periods for applying microwave energy for the gold layers of thicknesses of 1 nm, 2 nm, 3 nm, 4 nm, 5 nm, 6 nm, 7 nm, and 8 nm were 30 sec, 45 sec, 50 sec, 55 sec, 60 sec, 70 sec, and 75 sec, respectively.

The particle size of the gold nanoparticles formed on each of the glass substrates, which were denoted as S1, S2, S3, S4, S5, S6, S7, and S8, was determined using a scanning electron microscope, and the mean particle size of the gold nanoparticles formed on each of the glass substrates was measured. The results are shown in Table 1.

TABLE 1

| Samples | Thickness of a gold layer | Particle size of gold nanoparticles | Peak wavelength of extinction spectrum |
| --- | --- | --- | --- |
| S1 | 1 nm | 8 ± 3 nm | 532 nm |
| S2 | 2 nm | 13 ± 5 nm | 536 nm |
| S3 | 3 nm | 17 ± 7 nm | 542 nm |
| S4 | 4 nm | 23 ± 11 nm | 546 nm |
| S5 | 5 nm | 36 ± 13 nm | 550 nm |
| S6 | 6 nm | 47 ± 15 nm | 558 nm |
| S7 | 7 nm | 55 ± 19 nm | 568 nm |
| S8 | 8 nm | 70 ± 24 nm | 586 nm |

As shown in Table 1, the particle size of the gold nanoparticles may be controlled using gold layers of different thicknesses, and the peak wavelength of extinction spectrum varies according to the particle size of the gold nanoparticles. There is a linear relationship between the particle size of the gold nanoparticles and the thickness of the gold layer: $y=6.818x+0.154$, wherein y is the particle size of the gold nanoparticles, and x is the thickness of the gold layer. Other linear relationships may be obtained for the metallic nanoparticles made from a silver layer and an alloy layer of gold and silver. Therefore, in the present invention, the particle size of the metallic nanoparticles may be controlled using a metallic layer of a specific thickness.

Example 2

Detecting Streptavidin Using a Biosensor Chip

Three glass substrates formed with gold nanoparticles of different particles sizes were made according to Example 1, and were denoted as substrates A, B, and C, respectively. Substrate A was initially formed with a gold layer having a thickness of 2 nm and was subsequently formed with the gold nanoparticles having a particle size ranging from 8 to 18 nm. Substrate B was initially formed from a gold layer having a thickness of 4 nm and was subsequently formed with the gold nanoparticles having a particle size ranging from 12 to 34 nm. Substrate C was initially formed with a gold layer having a thickness of 6 nm and was subsequently formed with the gold nanoparticles having a particle size ranging from 32 to 62 nm. Radio-frequency atmosphere plasma was applied to a surface of each of substrates A, B, C to conduct a hydrophilic treatment. Each of substrates A, B, C was then immersed in an APTMS solution (1 mM) for 4 hr to crosslink APTMS onto the surfaces of the glass substrates via hydrolysis so as to form an APTMS film on the surface of each of the glass substrates.

Each of substrates A, B, C formed with the gold nanoparticles and the APTMS films was immersed in a solution of D-Biotin (Aldrich) in a mixture of 1-ethyl-3-(3-dimethylaminopropyl)carbodiimide and N-hydrosuccinimide. Biotin was attached a the APTMS film via amide bonding so as to form a biosensor chip having D-Biotin as a receptor for detecting streptavidin. The biosensor chips made from substrates A, B, and C were denoted as biosensor chips A, B, and C, respectively.

Figure 6:
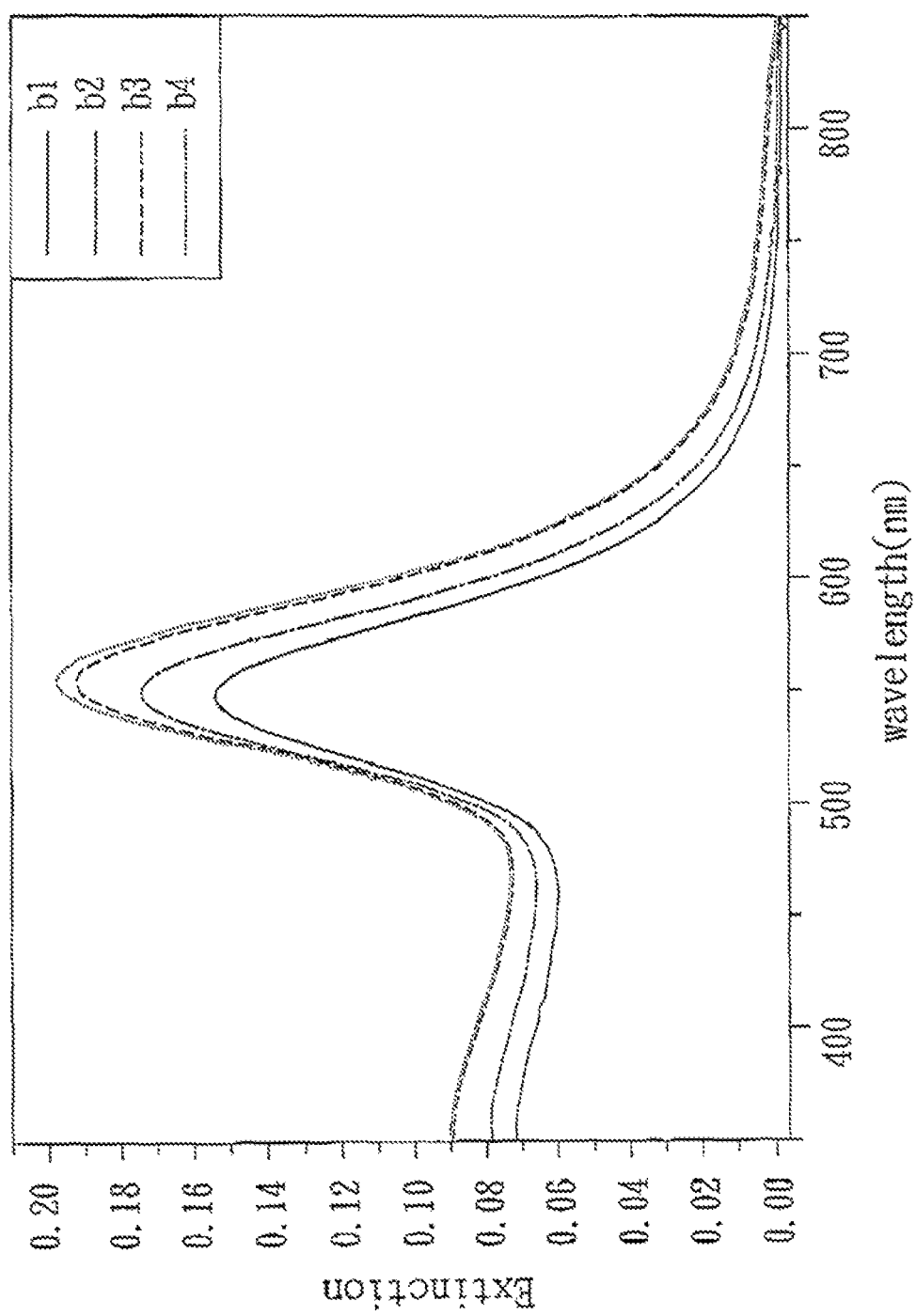
FIG. 6 is an extinction spectrum diagram of a second example of a biosensor chip according to the present invention at four different stages.
Figure 7:
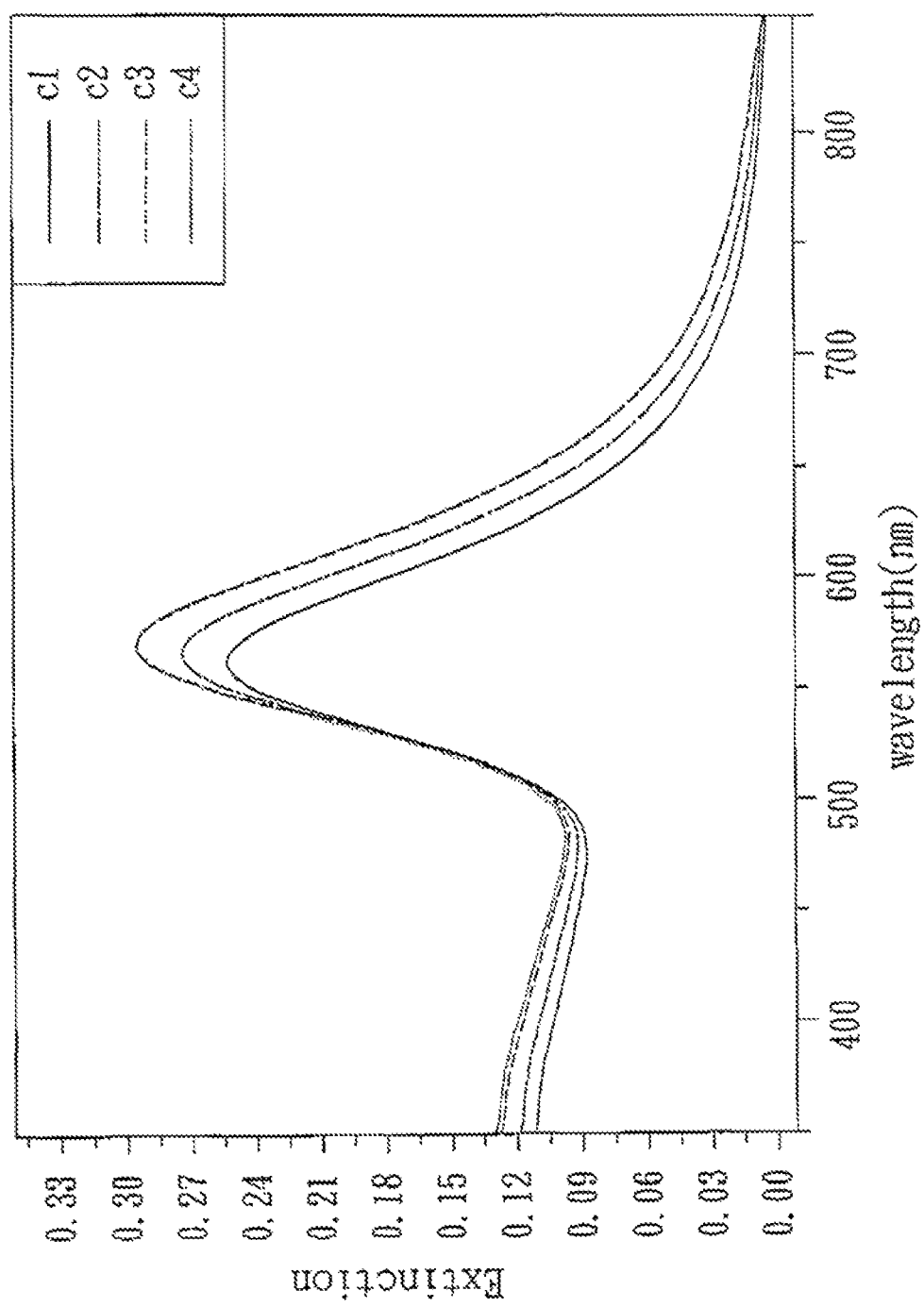
FIG. 7 is an extinction spectrum diagram of a third example of a biosensor chip according to the present invention at four different stages.

Extinction spectra of localized surface plasmon resonance for biosensor chips A, B, C at the following four different stages were obtained by irradiation with ultra-violet light and visible light: (I) the gold nanoparticles were formed on the glass substrate: (II) the APTMS film was formed on the glass substrate; (III) D-Biotin was attached to the APTMS film; and (IV) streptavidin was bonded to D-Biotin. The results are shown in FIGS. 5, 6, and 7.

Figure 5:
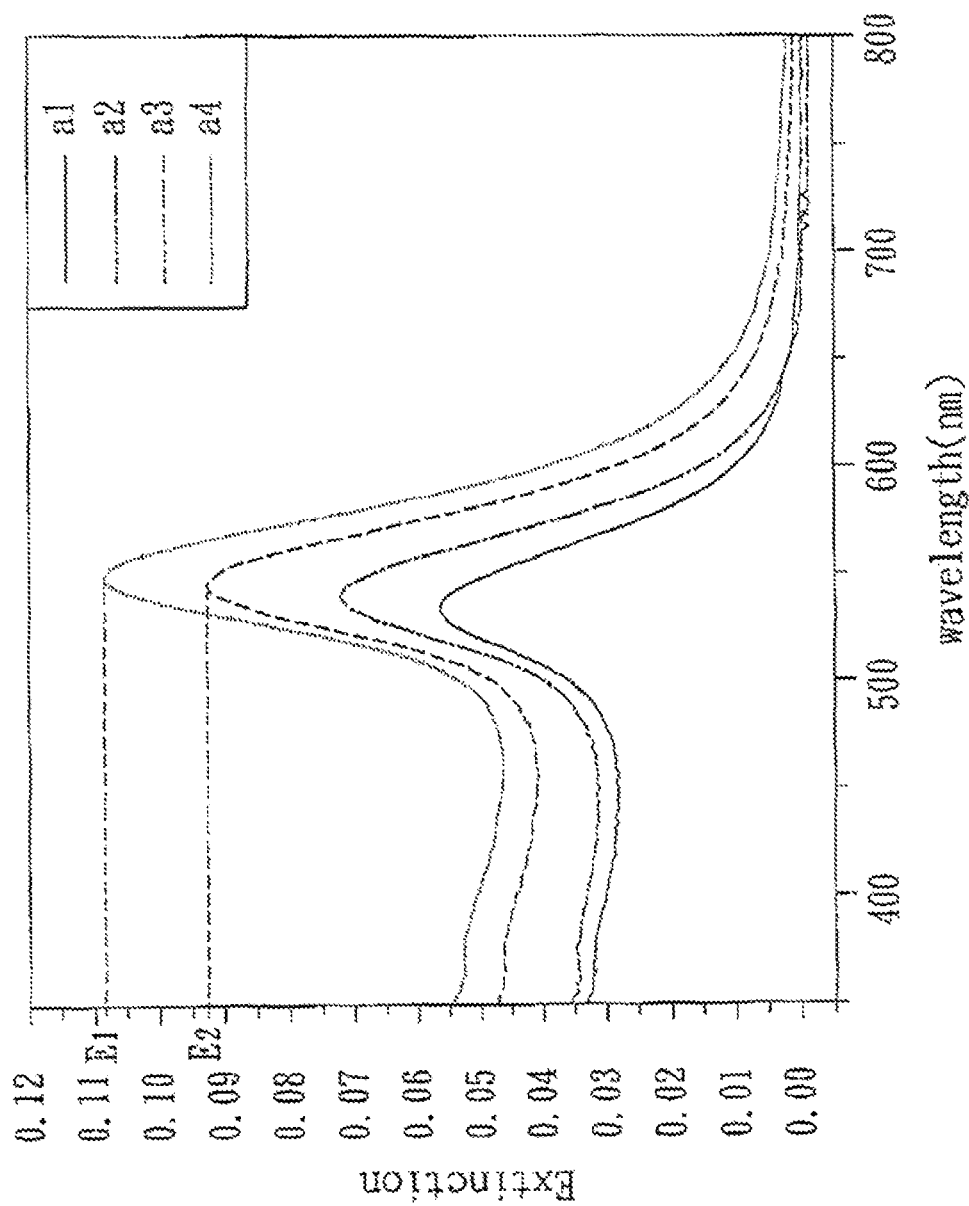
FIG. 5 is an extinction spectrum diagram of a first example of a biosensor chip according to the present invention four different stages.

In FIG. 5, curves a1, a2, a3, a4 indicate the extinction spectra for the biosensor chip A at stages (I), (II), (III), (IV), respectively. In FIG. 6, curves b1, b2, b3, b4 indicate the extinction spectra for the biosensor chip B at stages (I), (II), (III), (IV), respectively. In FIG. 7, curves c1, c2, c3, c4 indicate the extinction spectra for the biosensor chip C at stages (I), (II), (III), (IV), respectively.

As shown in FIG. 5, peak extinctions for curves a1, a2, a3 are significantly different from each other. The peak extinction of curve a2 is greater than that of curve a1, and the peak extinction of curve a3 is greater than that of curve a2. Similar results can be observed for curves b1, b2, b3 in FIG. 6 and curves c1, c2, c3 in FIG. 7. The results indicate that the extinction of the metallic nanoparticles may be affected by the surrounding environment of the metallic nanoparticles.

Comparing curve a3 with curve a4 in FIG. 5, peak wavelength of extinction spectrum shifts from 53 nm to 549 nm, and the peak extinction increases 17%, which is calculated according to $(E1-E2)/E2\times100\%$ (E1: peak extinction of curve a4, E2: peak extinction of curve a3). Comparing curves b3, b4 in FIG. 6, the peak extinction increases 3%. Comparing curves c3, c4 in FIG. 7, the peak extinction does not increase significantly. The results indicate that biosensor chip A, which contains the gold nanoparticles having a particle size ranging from 8 to 18 nm, has best sensitivity for detecting streptavidin, and that biosensor chip C, which contains the gold nanoparticles having a particle size ranging from 32 to 62 nm, has worst sensitivity for detecting streptavidin. In other words, generally, better sensitivity can be obtained with the biosensor chip containing relatively small metallic nanoparticles.

Example 3

Quantitative Analysis of Streptavidin Using the Biosensor Chip

Streptavidin samples were prepared in concentrations of 0 ng/ml, 10 ng/ml, 20 ng/ml, 30 ng/ml, 80 ng/ml, 120 ng/ml, 500 ng/ml, 1000 ng/ml, 5000 ng/ml, and 10000 ng/ml. Biosensor chip A fabricated in Example 2 was used for detecting the streptavidin samples. The results are shown in FIGS. 8 and 9.

Figure 8:
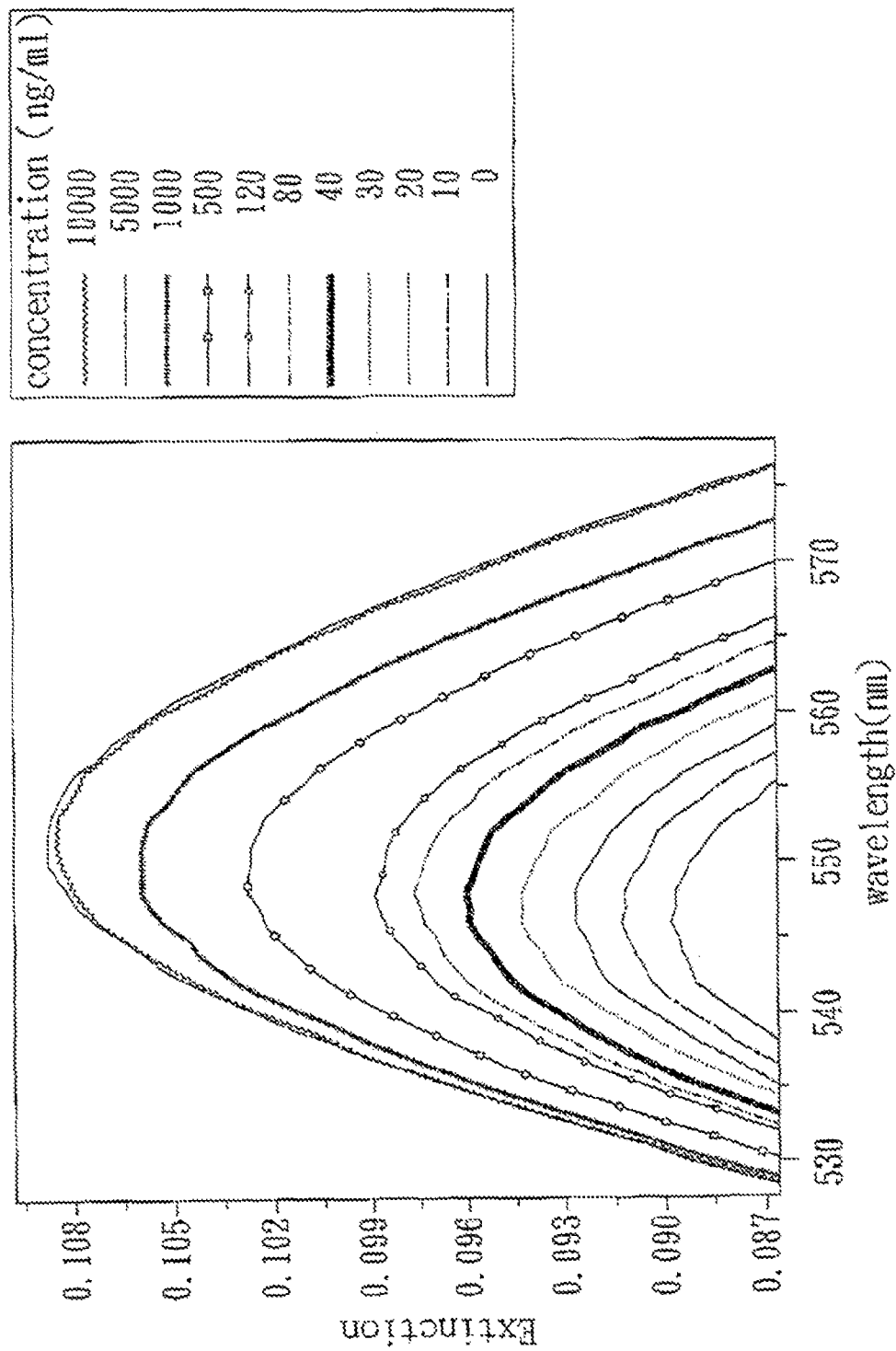
FIG. 8 is an extinction spectrum diagram of the first example of the biosensor chip for detecting streptavidin samples of various streptavidin concentrations.

As shown in FIG. 8, it is apparent that peak extinction increases with the concentration of streptavidin in the sample.

Figure 9:
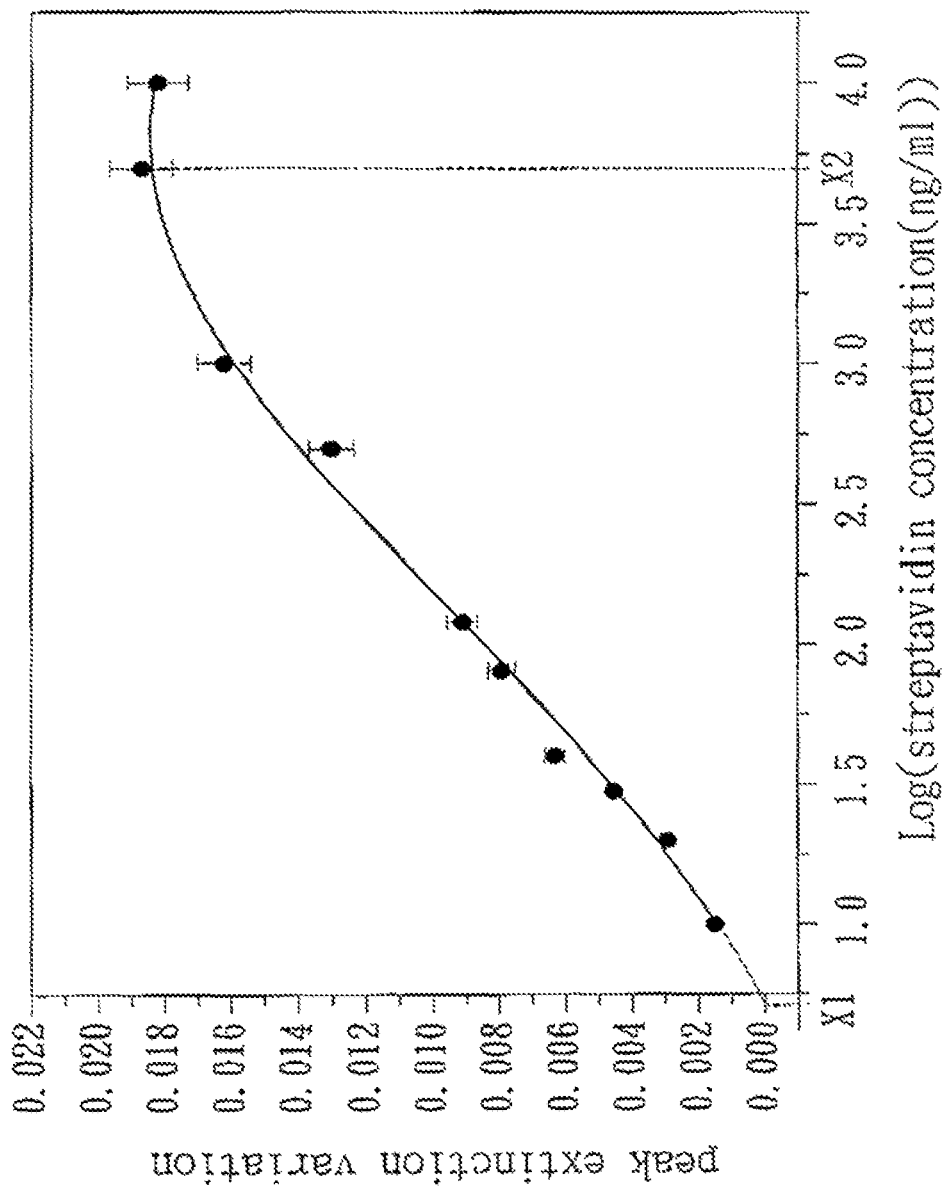
FIG. 9 is a plot of extinction variation versus log value of streptavidin concentration obtained from the detection result of FIG. 8.

As shown in FIG. 9, there is a generally linear relationship between peak extinction variation relative to peak extinction at a streptavidin concentration of 0 ng/ml and the log value of the streptavidin concentration. When the peak extinction variation is 0, the log value of the streptavidin concentration is about $-0.0088$ (X1), which corresponds to the streptavidin concentration of 0.98 ng/ml, which is the limit of detection for the biosensor chip A. The peak extinction variation reaches a plateau value when the log value of the streptavidin concentration increases to X2, which is about 3.7 and which corresponds to a streptavidin concentration of 5000 ng/ml (a saturation concentration which can be detected by biosensor chip A). Therefore, biosensor chip A can be used for detecting a wide range of streptavidin concentrations (i.e., from 0.98 to 5000 ng/ml), and has a great sensitivity (the limit of detection: 0.98 ng/ml).

Example 4

Detecting Anti-IgG Using a Biosensor Chip

Substrates A, B, and C used in Example 2 were used in this example. Each of substrates A, B, and C was treated with Harrick Plasma Cleaner for 5 min to conduct a hydrophilic treatment. Each of substrates A, B, and C was then immersed in an APTMS solution (10 mM) for 3 hr, rinsed with ethanol, PBS buffer solution, and deionized water, and dried with nitrogen gas to crosslink APTMS onto the surfaces of the glass substrates so as to form an APTMS film on the surface of each of the glass substrates.

Each of substrates A, B, and C formed with the gold nanoparticles and the APTMS films was immersed in a 10 w/w % glutaraldehyde solution at 20° C. for 1 hr. Glutaraldehyde was attached to the APTMS film via amide bonding. Each of the substrates A, B, and C was then treated with an aqueous mixture of 100 ppm IgG, 0.1 M EDC, and 0.05 M NHS in a PBS (pH7.4) solution at 20° C. for 12 hr, rinsed with PBS buffer solution and deionized water, and dried with nitrogen gas to immobilize IgG onto glutaraldehyde so as to farm a biosensor chip having IgG as a receptor for detecting anti-IgG. The biosensor chips made from substrates A, B, and C were denoted as biosensor chips A', B', and C', respectively.

Figure 11:
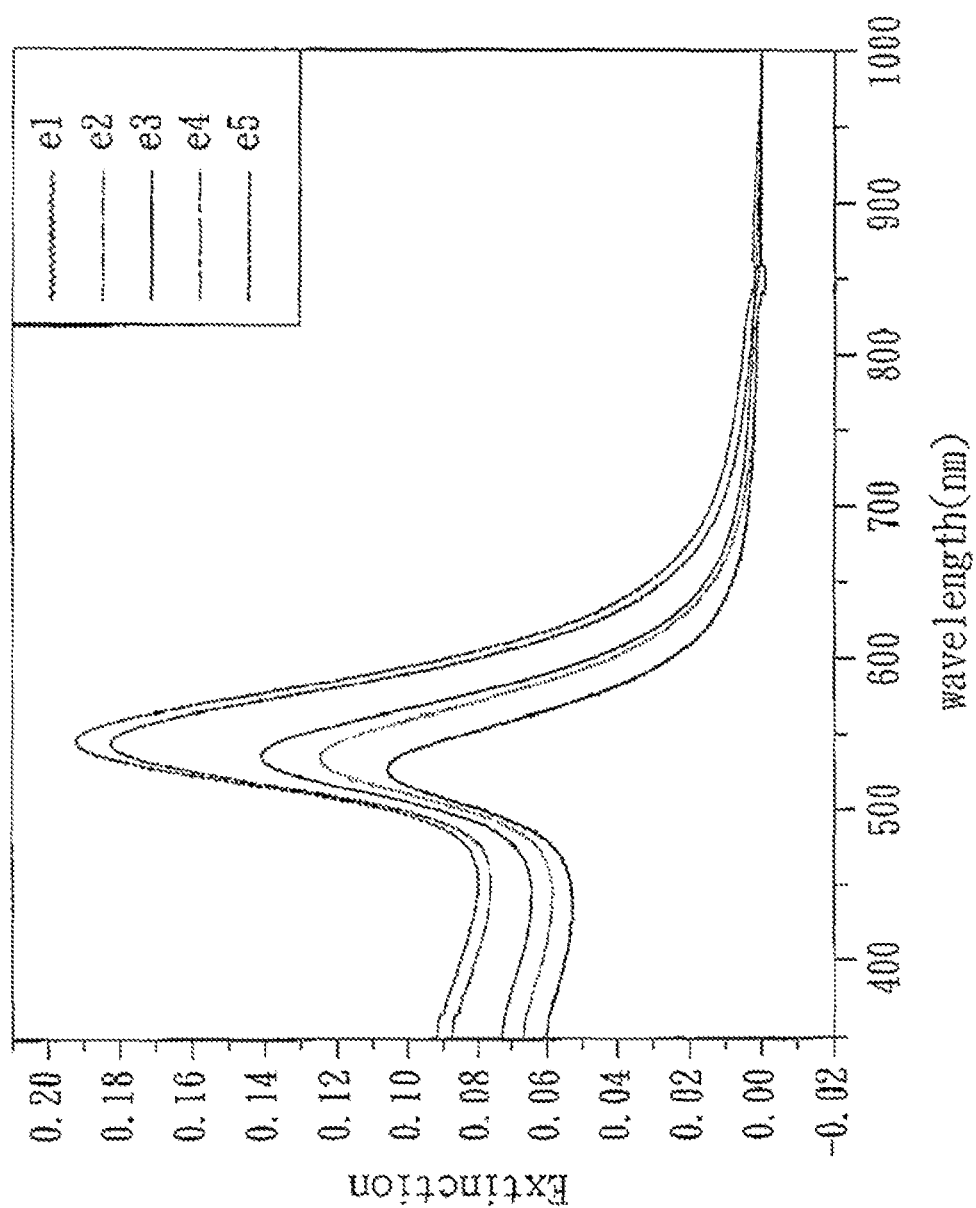
FIG. 11 is an extinction spectrum diagram of a fifth example of a biosensor chip according to the present invention at different stages.
Figure 12:
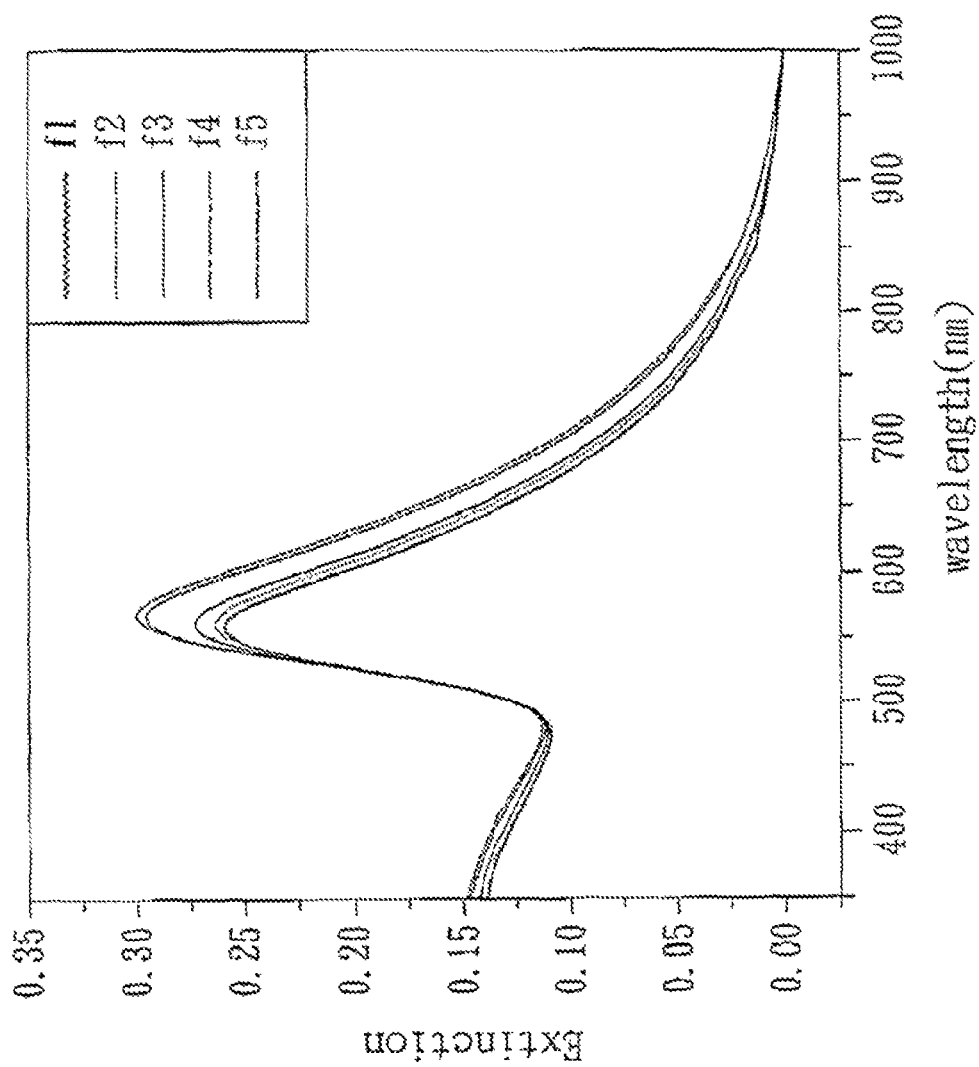
FIG. 12 is an extinction spectrum diagram of a sixth example of a biosensor chip according to the present invention at different stages.

Extinction spectra of localized surface plasmon resonance for biosensor chips A', B', and C' at the following different stages were obtained by irradiation with ultra-violet light and visible light: (I) the gold nanoparticles were formed on the glass substrate; (II) the APTMS film was formed on the glass substrate; (III) glutaraldehyde was attached to the APTMS film; (IV) IgG was immobilized onto glutaraldehyde; and (V) anti-IgG (2 ppm) was bonded to IgG. The results are shown in FIGS. 10, 11, and 12.

Figure 10:
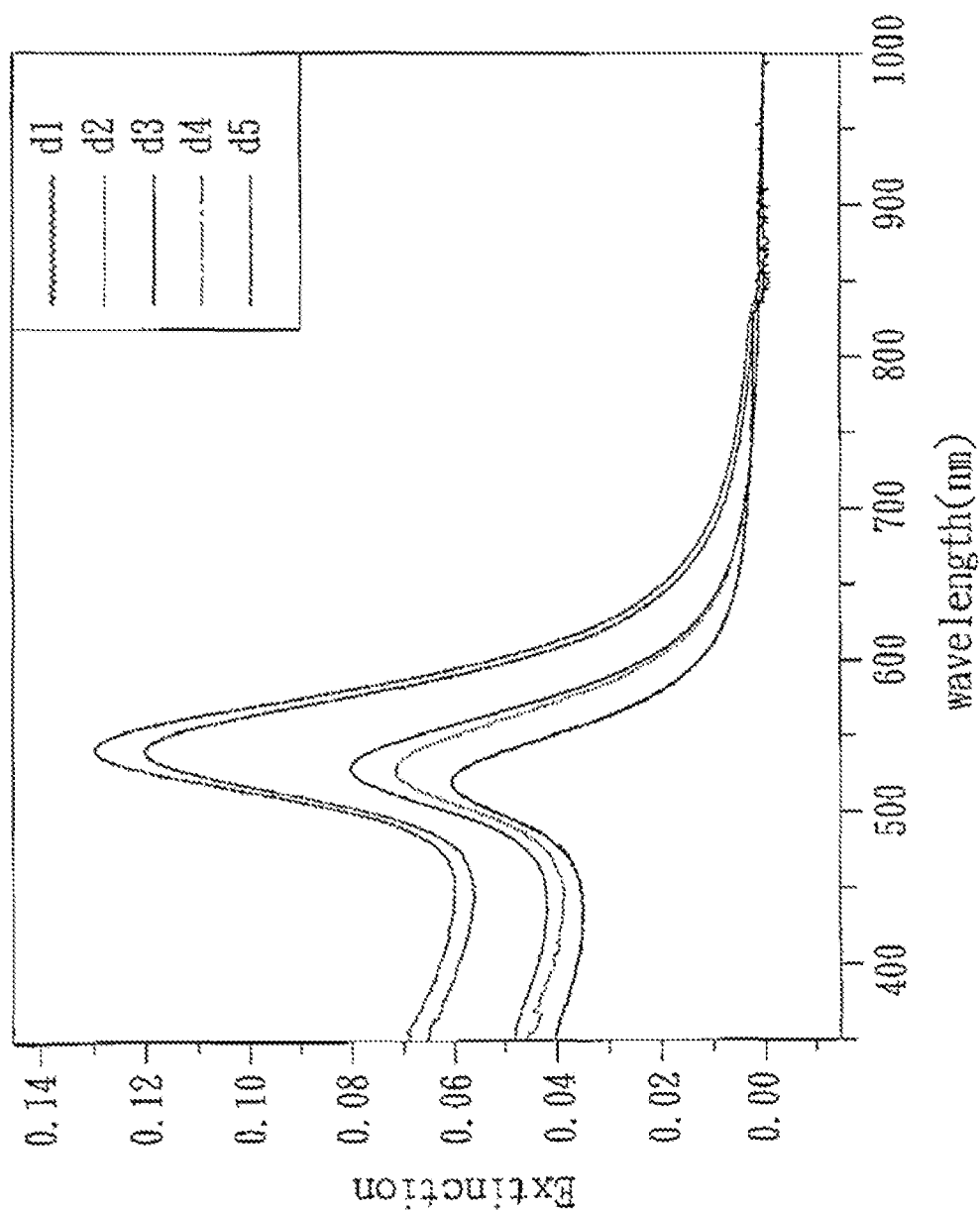
FIG. 10 is an extinction spectrum diagram of a fourth example of a biosensor chip according to the present invention at different stages.

In FIG. 10, curves d1, d2, d3, d4, and d5 indicate the extinction spectra for the biosensor chip A' at stages (I), (II), (III), (IV), and (V), respectively. In FIG. 11, curves e1, e2, e3, e4, and e5 indicate the extinction spectra for the biosensor chip B' at stages (I), (II), (III), (IV), and (V), respectively. In FIG. 12, curves f1, f2, f3, f4, and f5 indicate the extinction spectra for the biosensor chip C' at stages (I), (II), (III), (IV), and (V), respectively.

As shown in FIG. 10, peak extinctions for curves d1, d2, d3, and d4 are significantly different from each other. The peak extinction of curve d2 is greater than that of curve d1, the peak extinction of curve d3 is greater than that of curve d2, and the peak extinction of curve d4 is greater than that of curve d3. Similar results can be observed for curves e1, e2, e3, and e4 in FIG. 11 and curves f1, f2, f3, and f4 in FIG. 12. The results indicate that the extinction of the metallic nanoparticles may be affected by the surrounding environment of the metallic nanoparticles.

Comparing curve d4 with curve d5 in FIG. 10, the peak extinction increases about 8%, which is calculated according to $(0.1298-0.1203)/0.1203\times100\%$. Comparing curves e4 and e5 in FIG. 11, the peak extinction increases about 5%. Comparing curves f4 and f5 in FIG. 12, the peak extinction increases about 1.5%. Similar to the results of Example 2, the results indicate that biosensor chip A', which contains the gold nanoparticles having a particle size ranging from 8 to 18 nm, has best sensitivity for detecting anti-IgG, and that biosensor chip C', which contains the gold nanoparticles having a particle size ranging from 32 to 62 nm, has worst sensitivity far detecting anti-IgG. In other words, generally, better sensitivity can be obtained with the biosensor chic containing relatively small metallic nanoparticles.

Example 5

Quantitative Analysis of Anti-IgG Using the Biosensor Chip

Anti-IgG samples were prepared in concentrations of 0 ng/ml, 2 ng/ml, 4 ng/ml, 10 ng/ml, 20 ng/ml, 40 ng/ml, 0 ng/ml, 100 ng/ml, 200 ng/ml, 400 ng/ml, 800 ng/ml, 1000 ng/ml, and 20000 ng/ml. Biosensor chip A' fabricated in Example 4 was used for detecting the anti-IgG samples. The results are shown in FIGS. 13 and 14.

Figure 13:
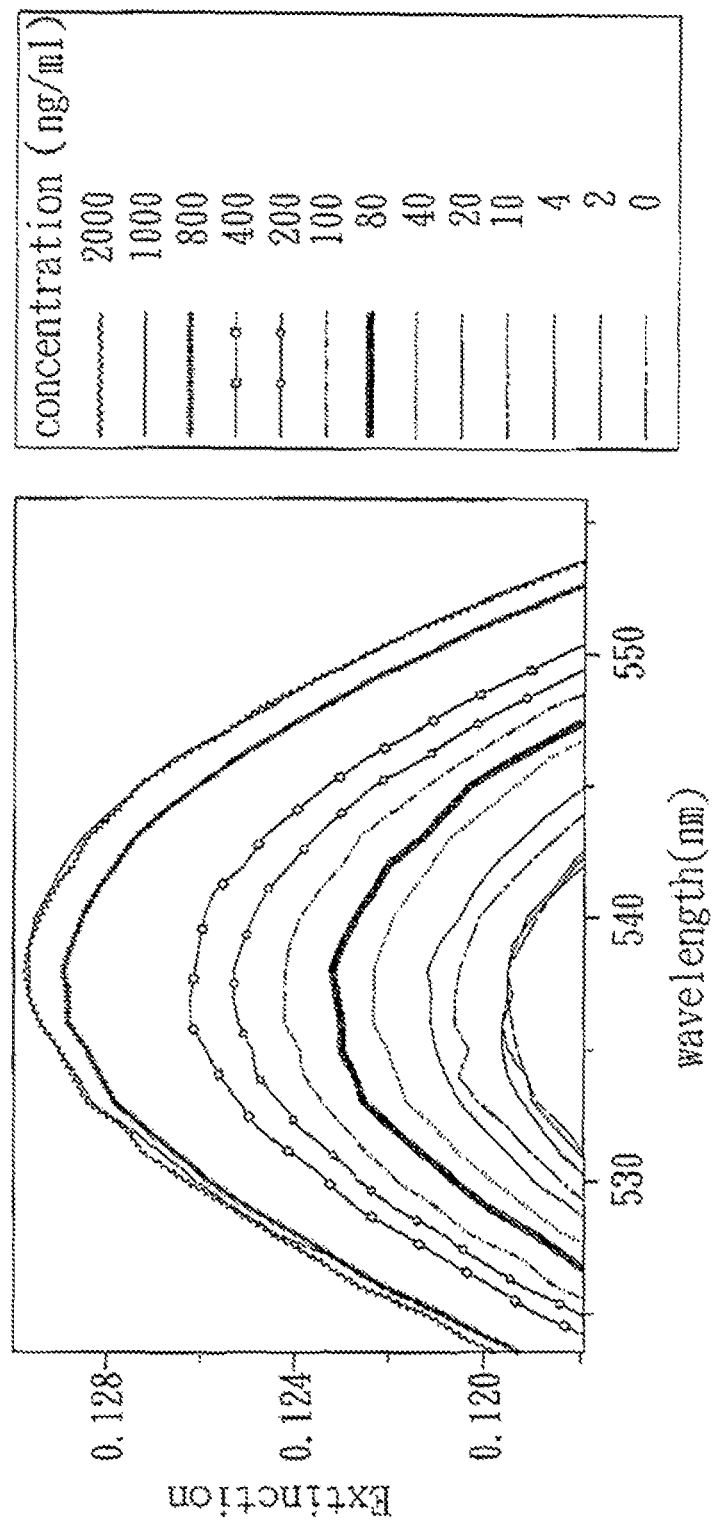
FIG. 13 is an extinction spectrum diagram of the fourth example of the biosensor chip for detecting anti-IgG samples of various anti-IgG concentrations.

As shown in FIG. 13, it is apparent that peak extinction increases with the concentration of anti-IgG in the sample.

Figure 14:
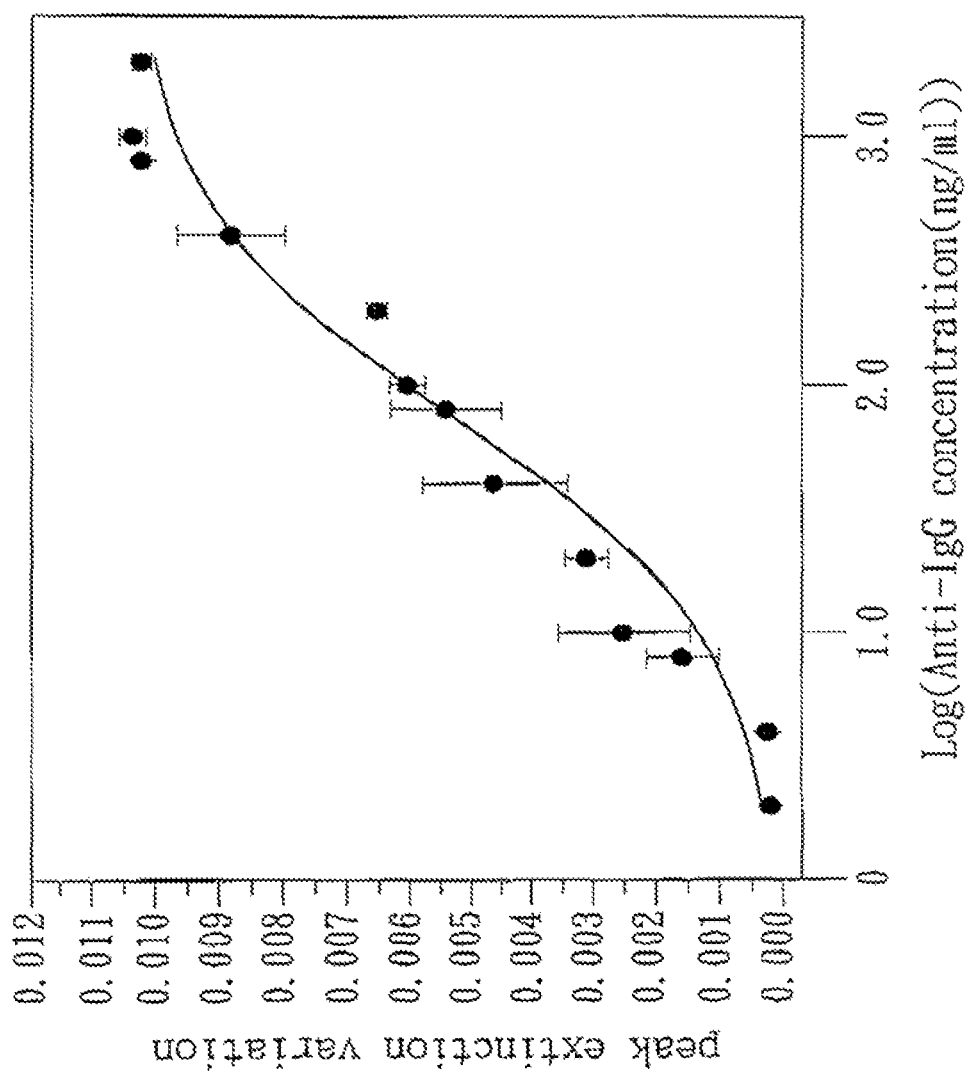
FIG. 14 is a plot of extinction variation versus log value of anti-IgG concentration obtained from the detection result of FIG. 13.

As shown in FIG. 14, there is a generally linear relationship between peak extinction variation relative to peak extinction at an anti-IgG concentration of 0 ng/ml and the log value of the anti-IgG concentration. When the peak extinction variation is 0, the log value of the anti-IgG concentration is about 1, which corresponds to the anti-IgG concentration of 10 ng/ml, which is the limit of detection for the biosensor chip A'. The peak extinction variation reaches a plateau value when the log value of the anti-IgG concentration increases to 3, which corresponds to an anti-IgG concentration of 1000 ng/ml (a saturation concentration which can be detected by biosensor chip A'). Therefore, biosensor chip A' can be used for detecting a range of anti-IgG concentrations (i.e., from 10 to 1000 ng/ml) and has a great sensitivity (the limit of detection: 10 ng/ml). In view of the aforesaid, the method of fabricating a biosensor chip of the present invention and the biosensor chip made thereby has the following advantages:

1. Compared to the peak extinction detected when the biosensor chip has yet to bind to the target analyte 50, the peak extinction detected after the biosensor chip binds to the t get analyte 50 varies, especially when the particle size of the metallic nanoparticles 3 of the biosensor chip is controlled to be within a specific range, for example, 5 nm to 20 nm. Therefore, the biosensor chip of the present invention may be used to qualitative detection of the target analyte 50.

2. The receptors 41 used in the biosensor chip of the present invention are selected according to the specific target analyte 50 to be detected. Therefore, the biosensor chip may be flexibly configured for detection of various target analytes.

3. In addition to qualitative detection, as described in the aforesaid Examples 3 and 5, the biosensor chip of the present invention may be used for quantitative detection of the concentration of the target analyte 50.

4. In the method of fabricating a biosensor the present invention, the metallic nanoparticles 3 having a predetermined particle size may be easily formed on the transparent substrate 2 using simple equipment. The biosensor chip may be fabricated by attaching the receptors 41 on the substrate 2 via the surface-modifier 42. Therefore, the biosensor chip may be fabricated easily and efficiently.

5. The metallic nanoparticles 3 are formed and bound stably on the surface 21 of the transparent substrate 2, and thus will not be affected by subsequent processing of the method of fabricating the biosensor chip and during the detection of the target analyte 50. Therefore, the biosensor chip of the present invention has a stable quality and may be reliably used for the detection of the target analyte 50.

6. The metallic nanoparticles 3 are formed and bound stably on the surface 21 of the transparent substrate 2 via a microwave plasma treatment. After the detection is completed, the biosensor chip may be cleaned using a proper buffer solution. For example, Glycine-HCl buffer solution may be used for dissociating streptavidin from biotin. Therefore, the biosensor chip of the present invention may be reused, and thus the operating cost may be reduced.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. A biosensor chip for detecting a target analyte comprising:
   a transparent substrate;
   metallic nanoparticles formed on a surface of said transparent substrate in a spaced apart manner and partly embedded in said transparent substrate;
   a surface-modifier attached to said surface of said transparent substrate among said metallic nanoparticles; and
   an analyte-specific receptor directly bound to said surface-modifier.

2. The biosensor chip of claim 1, wherein said metallic nanoparticles have an average diameter ranging from 5 nm to 20 nm.

3. The biosensor chip of claim 1, wherein said metallic nanoparticles have an average diameter ranging from 10 nm to 20 nm.

4. The biosensor chip of claim 1, wherein said metallic nanoparticles are made from a metal selected from the group consisting of gold, silver and gold alloy, and said transparent substrate is made from a material selected from the group consisting of glass, quartz, mica, sapphire and transparent ceramics.

5. The biosensor chip of claim 1, wherein said transparent substrate is made from glass, and said surface-modifier includes a silane compound.

6. The biosensor chip of claim 5, wherein said analyte-specific receptor includes 4-carboxybenso-15-crown-5.

7. The biosensor chip of claim 1, wherein said surface-modifier includes aminopropyltrimethoxysilane, and said analyte-specific receptor includes biotin.

8. The biosensor chip of claim 1, wherein said surface-modifier includes aminopropyltrimethoxysilane and glutaraldehyde, and said analyte-specific receptor includes immunoglobin G.

* * * * *